(12) United States Patent
Yopp et al.

(10) Patent No.: US 8,676,438 B2
(45) Date of Patent: Mar. 18, 2014

(54) METHOD AND SYSTEM FOR IMPLEMENTING ULTRASONIC SENSOR SIGNAL STRENGTH CALIBRATIONS

(71) Applicant: Ford Global Technologies, LLC, Dearborn, MI (US)

(72) Inventors: Wilford Trent Yopp, Canton, MI (US); Wangdong Luo, Auburn Hills, MI (US); Stephen Varghese Samuel, Troy, MI (US); Aric David Shaffer, Ypsilanti, MI (US); Vern Stempnik, Roseville, MI (US); Michael David Kane, Brighton, MI (US)

(73) Assignee: Ford Global Technologies, Dearborn, MI (US)

( * ) Notice: Subject to any disclaimer, the term of this patent is extended or adjusted under 35 U.S.C. 154(b) by 0 days.

(21) Appl. No.: 13/691,788

(22) Filed: Dec. 1, 2012

(65) Prior Publication Data

US 2014/0039750 A1    Feb. 6, 2014

Related U.S. Application Data

(63) Continuation-in-part of application No. 13/563,150, filed on Jul. 31, 2012.

(51) Int. Cl.
    *G01K 17/00*      (2006.01)
    *G01K 17/16*      (2006.01)

(52) U.S. Cl.
    USPC ............... 701/30.7; 701/31.1; 374/1; 73/649

(58) Field of Classification Search
    USPC ................... 701/30.5, 30.6, 30.7, 30.8, 31.1, 701/33.7–33.9; 374/1, 117, 119, 141, 144, 374/163; 73/1.82, 1.86, 649; 367/13
    See application file for complete search history.

(56) References Cited

U.S. PATENT DOCUMENTS

| | | | |
|---|---|---|---|
| 4,249,418 A | 2/1981 | Ebata | |
| 6,189,384 B1 * | 2/2001 | Piety et al. | 73/592 |
| 6,778,928 B2 * | 8/2004 | Stiller | 702/104 |
| 6,792,810 B2 | 9/2004 | Kupfernagel | |
| 7,343,803 B2 | 3/2008 | Triebl | |
| 7,421,321 B2 | 9/2008 | Breed | |
| 7,987,732 B2 | 8/2011 | Konzelmann | |
| 8,036,788 B2 | 10/2011 | Breed | |
| 8,081,539 B2 | 12/2011 | Faber | |
| 8,104,351 B2 | 1/2012 | Jung | |
| 8,166,824 B2 | 5/2012 | Sugiura | |
| 2010/0067324 A1 * | 3/2010 | Preissler | 367/13 |
| 2011/0248861 A1 * | 10/2011 | Corrado | 340/666 |
| 2011/0257860 A1 * | 10/2011 | Getman et al. | 701/70 |
| 2012/0090395 A1 | 4/2012 | Lavoie | |

* cited by examiner

*Primary Examiner* — Mary Cheung
*Assistant Examiner* — Rodney Butler
(74) *Attorney, Agent, or Firm* — Angela M. Brunetti; Frank MacKenzie

(57) ABSTRACT

Temperature compensation for ultrasonic sensors can have a significant error that is highly undesirable because temperature of ultrasonic sensors and the temperature of the medium through which they sense objects affect signal strength calibrations (e.g., echo thresholds) applied when detecting an object. In order to increase the detection capabilities and reported distance of an object, ultrasonic sensors need to adjust their detection criteria and distance calculations as the temperature of air surrounding a vehicle (i.e., outside air temperature) changes and also as the temperature of the sensor changes. Embodiments of the inventive subject matter provide for a simple, effective and consistent approach for determining a temperature upon which such detection criteria and distance calculation adjustments can be based.

24 Claims, 6 Drawing Sheets

METHOD AND SYSTEM FOR IMPLEMENTING ULTRASONIC SENSOR SIGNAL STRENGTH CALIBRATIONS

CROSS REFERENCE TO RELATED APPLICATIONS

This continuation-in-part patent application claims priority to co-pending U.S. Non-provisional patent application having Ser. No. 13/563,150; filed Jul. 31, 2012; entitled "Method And System For Implementing Ultrasonic Sensor Signal Strength Calibrations"; having a common applicant herewith; and being incorporated herein in its entirety by reference.

FIELD OF THE DISCLOSURE

The disclosures made herein relate generally to utilization of ultrasonic sensor data in automotive applications and, more particularly, to temperature compensating for improving performance of ultrasonic sensors in automotive applications.

BACKGROUND

It is well known that ultrasonic sensors are used for many driver aid applications to assist vehicle drivers. In such automotive applications, ultrasonic sensors use sound waves that pass through air (i.e. a fluid medium) to determine that an object is present and to determine its distance. One driver aid application is to detect an object of concern that the driver might not be aware of when the vehicle is backing up. Another driver aid application is to assist the driver in determining that an appropriate parking spot is available when the vehicle is in Park Assist mode. These driver aid applications are accomplished by using a plurality of ultrasonic sensors to detect objects and determine distance between such object and the sensor(s). Providing required information for these and other types of driver aid applications can necessitate mounting one or more of such ultrasonic sensors in close proximity to an engine compartment of the vehicle. For example, it is becoming common for a plurality of ultrasonic sensors to be mounted on a front bumper of a vehicle in addition to the well known mounting of a plurality of ultrasonic sensors in a rear bumper of the vehicle. However, unlike placement of the ultrasonic sensors in the rear bumper, ultrasonic sensors in the front bumper are typically exposed to heat from the engine compartment.

The ability of an ultrasonic sensor to detect objects and report their distance can be adversely impacted as the temperature of the outside air (i.e., temperature of outside air surrounding the vehicle) changes and/or temperature of the sensor(s) changes. For example, some ultrasonic sensors used in automotive applications begin exhibiting diminished object detection capability as the temperature of the sensor reaches about 40-50 degrees Celsius. To assist with mitigating such temperature based variability in sensing performance of such ultrasonic sensor(s), vehicle systems typically make use of the outside air temperature data that is used to display outside temperature to vehicle users to compensate for changes in temperature as it relates to ultrasonic sensor performance. The sensor used to determine the outside air temperature data (i.e., the outside air temperature sensor) can be located in or near to an engine compartment of a vehicle. For example, the outside air temperature sensor is often located on the grill or other forward structure of a vehicle. As a result, heat from an engine of the vehicle can affect accuracy of the ambient air temperature data provided by the outside air temperature sensor, especially when vehicle is standing still. To help prevent inaccuracies in outside air temperature data arising from engine heat, algorithms are used to counteract the effects of the engine heat by restricting the raise of the displayed outside air temperature. This restriction can result in an inaccurate estimation of the sensor's actual temperature.

Accordingly, temperature compensation for ultrasonic sensors can have a significant error that is highly undesirable because temperature of ultrasonic sensors and the temperature of the medium through which they sense objects affects signal strength calibrations (e.g., echo thresholds) applied when detecting an object. In order to increase the detection capabilities and reported distance of an object, ultrasonic sensors need to adjust their detection criteria and distance calculations as the temperature of air surrounding a vehicle (i.e., outside air temperature) changes and also as the temperature of the sensor changes. Therefore, a simple, effective and consistent approach for determining a temperature upon which such detection criteria and distance calculations adjustments can be based would be beneficial, desirable and useful.

SUMMARY OF THE DISCLOSURE

Embodiments of the inventive subject matter are directed to providing a more accurate estimation of a temperature of an ultrasonic sensor of a vehicle. In particular, embodiments of the inventive subject matter are directed to determining a temperature reference value upon which adjustments to detection criteria and distance calculations of an ultrasonic sensor mounted in or adjacent to a compartment of a vehicle having an elevated temperature (e.g., an engine compartment) or otherwise exposed to a heat source of a vehicle (e.g., an exhaust system component of the vehicle, road heat, etc). To this end, embodiments of the inventive subject matter advantageously use various available air temperature information and powertrain operating information in estimating a difference between outside air temperature and temperature of air that is elevated by operation and/or location of the vehicle (e.g., air within or escaping from an engine compartment of the vehicle, heat from a road surface, etc). This difference between the outside air temperature and elevated temperature air is provided to one or more ultrasonic sensors of the vehicle and/or control apparatus thereof for use in adjusting a signal strength calibration associated with the one or more ultrasonic sensors. As will be discussed below in greater detail, the signal strength calibration can include calibration information associated with signal reception sensitivity and/or calibration information associated with output power of an object sensing signal of the one or more ultrasonic sensors (e.g., increasing output power to maintain a uniform sound pressure level of the object sensing signal).

Embodiments of the inventive subject matter are beneficial in that they provide for a more accurate temperature of an ultrasonic sensor mounted in an environment of a vehicle that is subjected to excessive heat such as from an engine of a vehicle or pavement on which the vehicle is standing still. By more accurately determining the temperature of an ultrasonic sensor (e.g., the temperature of air surrounding or flowing over ultrasonic sensor), it is possible to provide improved sensor performance as it relates to object detection and distance reporting. To accomplish such improved object detection and distance reporting performance, embodiments of the inventive subject matter implement algorithms to estimate the ultrasonic sensor's temperature using various temperature information that is available from existing temperature sensors of the vehicle. In the specific example of an ultrasonic sensor that is mounted in or near an engine compartment of the vehicle and that is exposed to outside airflow when the vehicle is moving, an estimate of the ultrasonic sensor's temperature can be made using a signal from various available air temperature information (e.g., filtered and/or unfiltered outside air temperature) and/or powertrain operating information (e.g., coolant temperature, intake air temperature, radiator grille block position, vehicle speed, etc).

In one embodiment of the inventive subject matter, a method for processing a signal provided from an ultrasonic sensor of a vehicle to a signal processing unit of the vehicle comprises a plurality of operations. An operation is performed for determining a first instance of a signal strength calibration. The first instance of the signal strength calibration is based on a first instance of outside air temperature information and a first instance of powertrain operating information. The signal strength calibration enables information outputted from the ultrasonic sensor to provide at least a baseline level of object detecting performance. An operation is performed for determining a vehicle operating condition requiring alteration of the signal strength calibration for maintaining at least the baseline level of object detecting performance from the information outputted from the ultrasonic sensor. In response to determining the vehicle operating condition requiring alteration of the signal strength calibration, an operation is performed for determining a second instance of the signal strength calibration. The second instance of the signal strength calibration is based at least one of a second instance of the outside air temperature information and a second instance of the powertrain operating information. The second instance of the signal strength calibration enables the information outputted from the ultrasonic sensor to provide at least the baseline level of object detecting performance. One or more one data processing devices access, from memory coupled to the one or more data processing devices, instructions for causing the one or more data processing devices to carry out such operations.

In another embodiment of the inventive subject matter, an electronic controller system of a vehicle has at least one data processing device coupled between an ultrasonic sensor, a signaling apparatus configured for outputting outside air temperature information and a signaling apparatus configured for outputting powertrain operating information. The electronic controller system has a set of instructions tangibly embodied on a non-transitory processor-readable medium thereof. The set of instructions are accessible from the non-transitory processor-readable medium by the at least one data processing device of the electronic controller system for being interpreted thereby. The set of instructions is configured for causing the at least one data processing device to carry out an operation for providing the signal processing unit with a first instance of a signal strength calibration. The first instance of the signal strength calibration is based on a first instance of outside air temperature information and a first instance of powertrain operating information. The signal strength calibration enables information outputted from the ultrasonic sensor to provide at least a baseline level of object detecting performance. The set of instructions is configured for causing the at least one data processing device to carry out an operation for determining a vehicle operating condition requiring alteration of the signal strength calibration for maintaining at least the baseline level of object detecting performance from the information outputted from the ultrasonic sensor. The set of instructions is configured for causing the at least one data processing device to carry out an operation for providing the signal processing unit with a second instance of the signal strength calibration in response to determining the vehicle operating condition requiring alteration of the signal strength calibration. The second instance of the signal strength calibration is based at least one of a second instance of the outside air temperature information and a second instance of the powertrain operating information. The second instance of the signal strength calibration enables the information outputted from the ultrasonic sensor to provide at least the baseline level of object detecting performance.

In another embodiment of the inventive subject matter, a vehicle comprises an ultrasonic sensor, a first signaling apparatus configured for outputting outside air temperature information, a second signaling apparatus configured for outputting powertrain operating information and a signal processing unit coupled between the ultrasonic sensor, the first signaling apparatus and the second signaling apparatus. The signal processing unit includes at least one data processing device and a non-transitory processor-readable medium coupled thereto. The non-transitory processor-readable medium memory has a set of instructions tangibly embodied thereon. The set of instructions is accessible from the non-transitory processor-readable medium by the at least one data processing device for being interpreted thereby. The set of instructions is configured for causing the at least one data processing device to determine a first instance of a signal strength calibration. The first instance of the signal strength calibration is based on a first instance of outside air temperature information and a first instance of powertrain operating information. The signal strength calibration enables information outputted from the ultrasonic sensor to provide at least a baseline level of object detecting performance. The set of instructions is configured for causing the at least one data processing device to determine a vehicle operating condition requiring alteration of the signal strength calibration for maintaining at least the baseline level of object detecting performance from the information outputted from the ultrasonic sensor. The set of instructions is configured for causing the at least one data processing device to determine a second instance of the signal strength calibration in response to the set of instructions is configured for causing the at least one data processing device to determine the vehicle operating condition requiring alteration of the signal strength calibration. The second instance of the signal strength calibration is based at least one of a second instance of the outside air temperature information and a second instance of the powertrain operating information. The second instance of the signal strength calibration enables the information outputted from the ultrasonic sensor to provide at least the baseline level of object detecting performance.

These and other objects, embodiments, advantages and/or distinctions of the inventive subject matter will become readily apparent upon further review of the following specification, associated drawings and appended claims.

DETAILED DESCRIPTION OF THE DRAWING FIGURES

Figure 1:
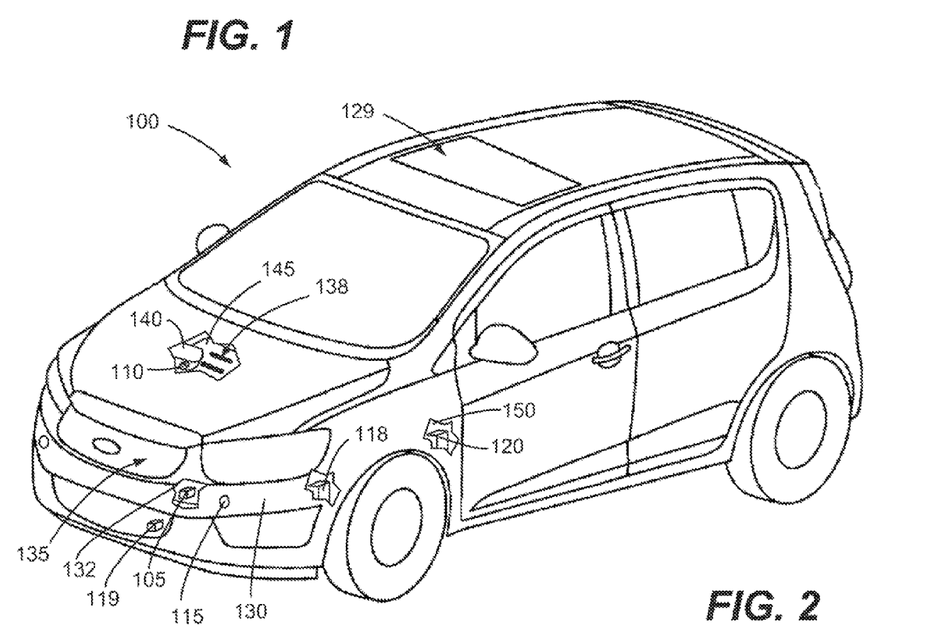
FIG. 1 is a illustrative view showing a vehicle configured in accordance with an embodiment of the inventive subject matter.
Figure 2:
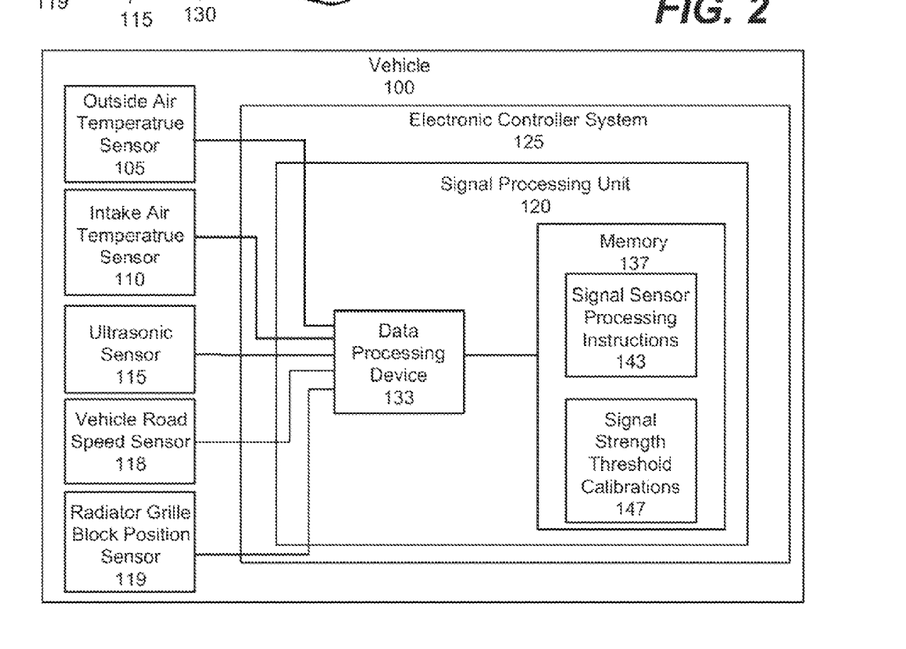
FIG. 2 is a block diagram showing functional elements of the vehicle of FIG. 1.

FIGS. 1 and 2 is a vehicle 100 configured in accordance with an embodiment of the inventive subject matter. The vehicle 100 includes an outside air temperature sensor 105 (i.e., a first sensor), an intake air temperature sensor 110 (i.e., a second sensor), an ultrasonic sensor 115 (i.e., a third sensor), a vehicle road speed sensor 118 (i.e., a fourth sensor), a radiator grille block position sensor 119, and a signal processing unit 120. The signal processing unit is connected to (e.g., between) the outside air temperature sensor 105, the intake air temperature sensor 110, the ultrasonic sensor 115, and the vehicle road speed sensor 118. The signal processing unit 120 can be an integral component of an electronic controller system 125 (shown in FIG. 2) that implements and/or supports control of a variety of different functional systems of the vehicle 100.

The outside air temperature sensor 105 can be mounted at a location between an occupant cabin 129 of the vehicle 100 and a front bumper cover 130 of the vehicle 100 such as, for example, on a bumper cover support 132 within or immediately adjacent to a front grill opening 135 of the vehicle 100. The outside air temperature sensor 105 outputs a signal characterizing a temperature of air surrounding of the vehicle 100. In particular, the outside air temperature sensor 105 outputs a signal characterizing a temperature of air surrounding or flowing over a front bumper cover 130 of the vehicle 100 (i.e., at least a portion of this air surrounds the occupant cabin 129). In this regard, when the vehicle 100 is at or above a sufficient road speed for a suitable duration of time, the outside air temperature sensor 105 is outputting a signal corresponding to ambient air surrounding the vehicle (i.e., an accurate reflection of outside air surrounding the vehicle). However, when the vehicle 100 is standing still for a suitably long period of time, the signal outputted by the outside air temperature sensor 105 can be influenced by heat from within an engine compartment 138 of the vehicle 100. Mounting locations of outside air temperature sensors and operability thereof are well known and are not unnecessarily limited in regard to embodiments of the inventive subject matter. The outside air temperature sensor 105 is an example of a signaling apparatus configured for outputting outside air temperature information.

The intake air temperature sensor 110 can be mounted on an air intake portion 140 of an engine 145 of the vehicle 100 such as, for example, an intake manifold, an air duct, and air filter housing, etc. The intake air temperature sensor 110 outputs a signal characterizing a temperature of air being inducted by the engine 145. The intake air temperature sensor 110 position within the engine compartment 138 and/or a location of an air inlet results of the air intake portion 140 results in the intake air temperature sensor 110 outputting a signal corresponding to a temperature of air within the engine compartment 138 when the vehicle 100 is stationary or moving sufficiently slow for a suitable duration of time. This location of the intake air temperature sensor 110 can result in a more accurate reading of air temperature within the engine compartment 138, particularly when the outside air temperature sensor 105 has a relatively less direct exposure to air from within the engine compartment 138 than does the intake air temperature sensor 110. Mounting locations of intake air temperature sensors and operability thereof are well known and are not unnecessarily limited in regard to embodiments of the inventive subject matter.

The ultrasonic sensor 115 is preferably a front facing sensor that is mounted on a front structure of the vehicle 100 such as, for example, the front bumper cover 130 and the bumper cover support 132. In such a mounted configuration, the ultrasonic sensor 115 will be exposed to heated air from within the engine compartment 138 when the vehicle 100 is stationary or moving sufficiently slow for a suitable duration of time. As such, temperature of the ultrasonic sensor 115 is subject to significant changes based on speed of the vehicle 100 and changes in temperature of air within the engine compartment 138. Mounting locations of ultrasonic sensors and operability thereof are well known and are not unnecessarily limited in regard to embodiments of the inventive subject matter.

The vehicle speed sensor 118 provides the function of outputting a signal corresponding to a road speed of the vehicle 100. To this end, the vehicle speed sensor 118 can be implemented in a variety of fashions. In one implementation, the vehicle speed sensor 118 can be a physical speed sensor that is mounted on a transmission of the vehicle 100 for obtaining vehicle road speed information therefrom. In another implementation, the vehicle speed sensor 118 can be a logical sensor that is integral with a global positioning system (GPS) of the vehicle 100. Mounting locations of vehicle road speed sensors and operability thereof are well known and are not unnecessarily limited in regard to embodiments of the inventive subject matter.

The signal processing unit 120 is configured for determining a distance between the ultrasonic sensor 115 (or other designated reference location) and an object adjacent to the vehicle 100. Such determination is performed in accordance with a signal strength calibration of the signal processing unit 120 as a function of the signal of the ultrasonic sensor 115. Advantageously, embodiments of the inventive subject matter are beneficial in that they provide for a more accurate temperature of an ultrasonic sensor mounted in an environment of a vehicle that is subjected to excessive heat such as from an engine of a vehicle or pavement on which the vehicle is standing still. By more accurately determining the temperature of an ultrasonic sensor, it is possible to provide improved sensor performance as it relates to object detection and distance reporting via selective ultrasonic sensor calibration based on temperature of the ultrasonic sensor. It is disclosed herein that, in conjunction with such temperature-dependent adjustment of the signal strength calibration, a strength of an emitted signal of the ultrasonic sensor 115 can be increased as a function of an increase in its temperature for the purposed of enhancing detecting of the reflected signal.

As will be discussed below in greater detail, the signal processing unit 120 provides the function of processing signals from the outside air temperature sensor 105, the intake air temperature sensor 110, the ultrasonic sensor 115, the vehicle speed sensor 118, and the radiator grille block position sensor 119 for enabling ultrasonic sensor calibrating functionality in accordance with the inventive subject matter to be implemented. The signal processing unit 120 can be mounted on a chassis structure 150 of the vehicle 100. Mounting locations of outside air temperature sensors, intake air temperature sensors, ultrasonic sensors, vehicle road speed sensors, and a signal processing unit 120 are well known and are not unnecessarily limited in regard to embodiments of the inventive subject matter. In this regard, the outside air temperature sensor 105, the intake air temperature sensor 110, the ultrasonic sensor 115, the vehicle speed sensor 118, and the radiator grille block position sensor 119 are individually and jointly an example of a second signaling apparatus configured for outputting powertrain operating information.

As shown in FIG. 2, in one embodiment, the signal processing unit 120 includes a data processing device 133 and memory 137 coupled to the data processing device 133. Sensor signal processing instructions 143 and signal strength threshold calibrations 147 are accessibly by the data processing device 133 from the memory 137. In this regard, a skilled person will appreciate methods, processes and/or operations configured for carrying out ultrasonic sensor calibrating functionality as disclosed herein are tangibly embodied by a computer readable medium having instructions thereon that are configured for carrying out such functionality.

Figure 3:
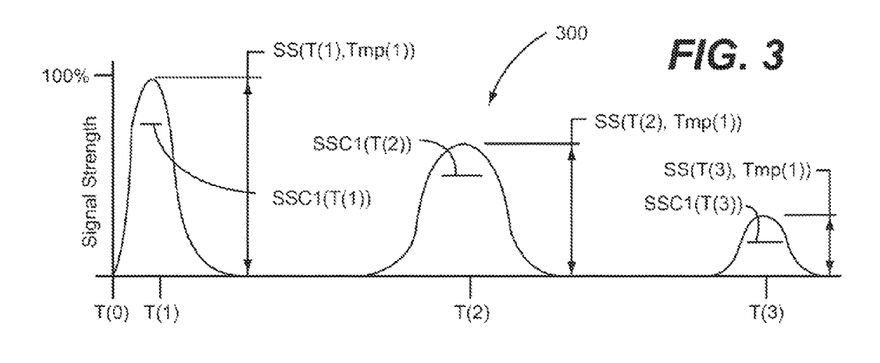
FIG. 3 is a graph showing an illustrative representation of acoustic response characteristics for a signal outputted by the ultrasonic sensor of FIG. 1 corresponding to a first signal strength calibration with the ultrasonic sensor being maintained at a first ultrasonic sensor temperature.
Figure 4:
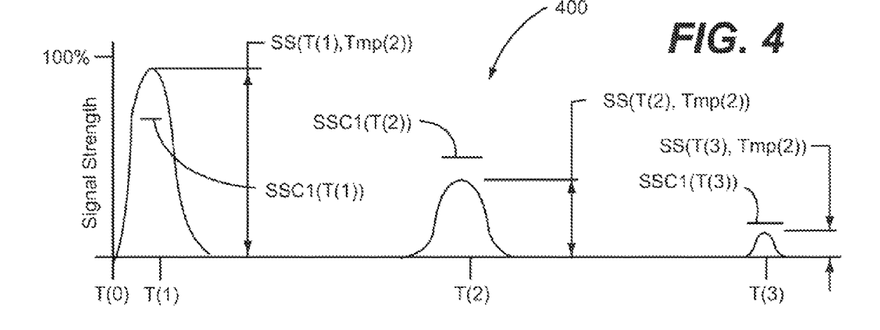
FIG. 4 is a graph showing an illustrative representation of acoustic response characteristics for a signal outputted by the ultrasonic sensor of FIG. 1 corresponding to the first signal strength calibration SSC1 with the ultrasonic sensor being maintained at a second ultrasonic sensor temperature that is greater than the first ultrasonic sensor temperature.
Figure 5:
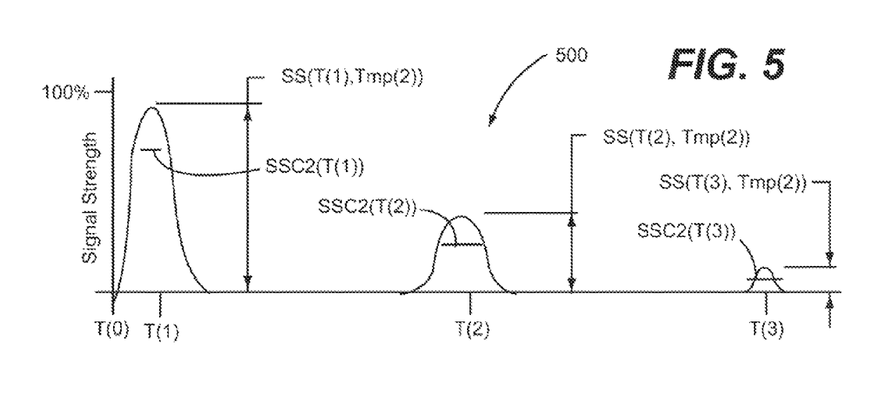
FIG. 5 is a graph showing an illustrative representation of acoustic response characteristics for a signal outputted by the ultrasonic sensor of FIG. 1 corresponding to a second signal strength calibration with the ultrasonic sensor being maintained at the second ultrasonic sensor temperature.

Referring now to FIGS. 3-5, object sensing characteristics of a typical ultrasonic sensor as a function of distance and sensor temperature are shown. As is well known, such a typical ultrasonic sensor will emit an acoustic signal of a known frequency and intensity and then sense energy of a reflected acoustic signal generated by the emitted acoustic signal impinging upon and reflecting from an object spaced away from the ultrasonic sensor. By knowing a total round trip time of the emitted and reflected acoustic signals (i.e., time from the sensor to an object being upon which the signal impinges and the time from the object back to the sensor), a distance between the sensor and the object can be determined (i.e., using known constants such as speed of sound through a fluid medium through which the signal is travelling). The ultrasonic sensor will output an electrical signal characterizing energy of the reflected acoustic signal. Examples of such a typical ultrasonic sensor, which are commonly used in automotive applications of object detection and distance ranging, are disclosed in U.S. Pat. Nos. 8,104,351; 8,081,539; 7,343,803; and 6,792,810. The inventive subject matter is not unnecessarily limited to any particular ultrasonic sensor or configuration of ultrasonic sensor.

FIG. 3 is a graph 300 showing an illustrative representation of acoustic response characteristics for a signal outputted by the ultrasonic sensor corresponding to a first signal strength calibration SSC1 (i.e., relatively low sensitivity calibration with respect to available signal strength calibrations) with the ultrasonic sensor being maintained at a first ultrasonic sensor temperature Tmp(1) such as, for example, 25 degrees C. The electrical signal outputted by the ultrasonic sensor represents a relative level of energy within the reflected acoustic signal for the given sensor temperature and signal strength calibration and for a baseline signal output energy. As can be seen, for the given temperature, calibration, and signal output energy conditions, the signal strength calibration values SSC1(T(1)), SSC1(T(2)) and SSC1(T(3)) at reflected acoustic signal propagation times T(1), T(2) and T(3), respectively, are well below the peak signal strengths SS(T(1)), SS(T(2)) and SS(T(3)) at such times. The reflected acoustic signal propagation time T(0) preferably, but not necessarily, represents a time at which the ultrasonic sensor is energized for causing the emitted acoustic signal to be emitted therefrom. The signal strength calibration values represent a signal strength level at a designated acoustic signal propagation time required for a reflected acoustic signal sensed by the ultrasonic sensor at the same to be designated acoustic signal propagation time to be recorded/recognized as a sensed instance of an object. Therefore, the ultrasonic sensor can provide acceptable signal sensing performance at the given temperature and calibration parameters over sensing distances corresponding to reflected acoustic signal propagation times T(1), T(2) and T(3). In this regard, the signal strength calibration of FIG. 3 is one that enables information outputted from the ultrasonic sensor to provide at least a baseline level of object detecting performance.

FIG. 4 is a graph 400 showing an illustrative representation of acoustic response characteristics for a signal outputted by the ultrasonic sensor corresponding to the first signal strength calibration SSC1 with the ultrasonic sensor being maintained at a second ultrasonic sensor temperature Tmp(2) such as, for example, 50 degrees C. The electrical signal outputted by the ultrasonic sensor represents a relative level of energy within the reflected acoustic signal for the given sensor temperature and signal strength calibration and for the same baseline emitted acoustic signal strength used in association with the illustrative representation of FIG. 3. As can be seen, for the given temperature, calibration, and signal output energy conditions, the signal strength calibration value SSC1(T(1)) at reflected acoustic signal propagation time T(1) is acceptably below the peak signal strength at reflected acoustic signal propagation time T(1). However, for the given temperature, calibration, and signal output energy conditions, the signal strength calibration values SSC1(T(2)) and SSC1(T(3)) at reflected acoustic signal propagation times T(2) and T(3), respectively, are not acceptably below the peak signal strength at reflected acoustic signal propagation times T(1) and T(2)). Therefore, the ultrasonic sensor can provide acceptable signal sensing performance at the given temperature and calibration parameters over sensing distance corresponding to reflected acoustic signal propagation time T(1), but not over sensing distances corresponding to reflected acoustic signal propagation times T(2) and T(3). The resulting performance of the ultrasonic sensor at the conditions of FIG. 4 would be underreporting of objects at distances corresponding to reflected acoustic signal propagation times T(2) and T(3).

FIG. 5 is a graph 500 showing an illustrative representation of acoustic response characteristics for a signal outputted by the ultrasonic sensor corresponding to a second signal strength calibration SSC2 (i.e., relatively high sensitivity calibration with respect to the first signal strength calibration) with the ultrasonic sensor being maintained at the second ultrasonic sensor temperature Tmp(2) such as, for example, 50 degrees C. The electrical signal outputted by the ultrasonic sensor represents a relative level of energy within the reflected acoustic signal for the given sensor temperature and signal strength calibration and for the same baseline emitted acoustic signal strength used in association with the illustrative representations of FIGS. 3 and 4. As can be seen, for the given temperature, calibration, and signal output energy conditions, the signal strength calibration values SSC2(T(1)), SSC2(T(2)) and SSC2(T(3)) at reflected acoustic signal propagation times T(1), T(2) and T(3), respectively, are well above the peak signal strengths at such times. Therefore, the ultrasonic sensor can provide acceptable signal sensing performance at the given temperature and calibration parameters over sensing distances corresponding to reflected acoustic signal propagation times T(1), T(2) and T(3). In this regard, the signal strength calibration of FIG. 5 is one that enables information outputted from the ultrasonic sensor to provide at least a baseline level of object detecting performance.

Figure 6A:
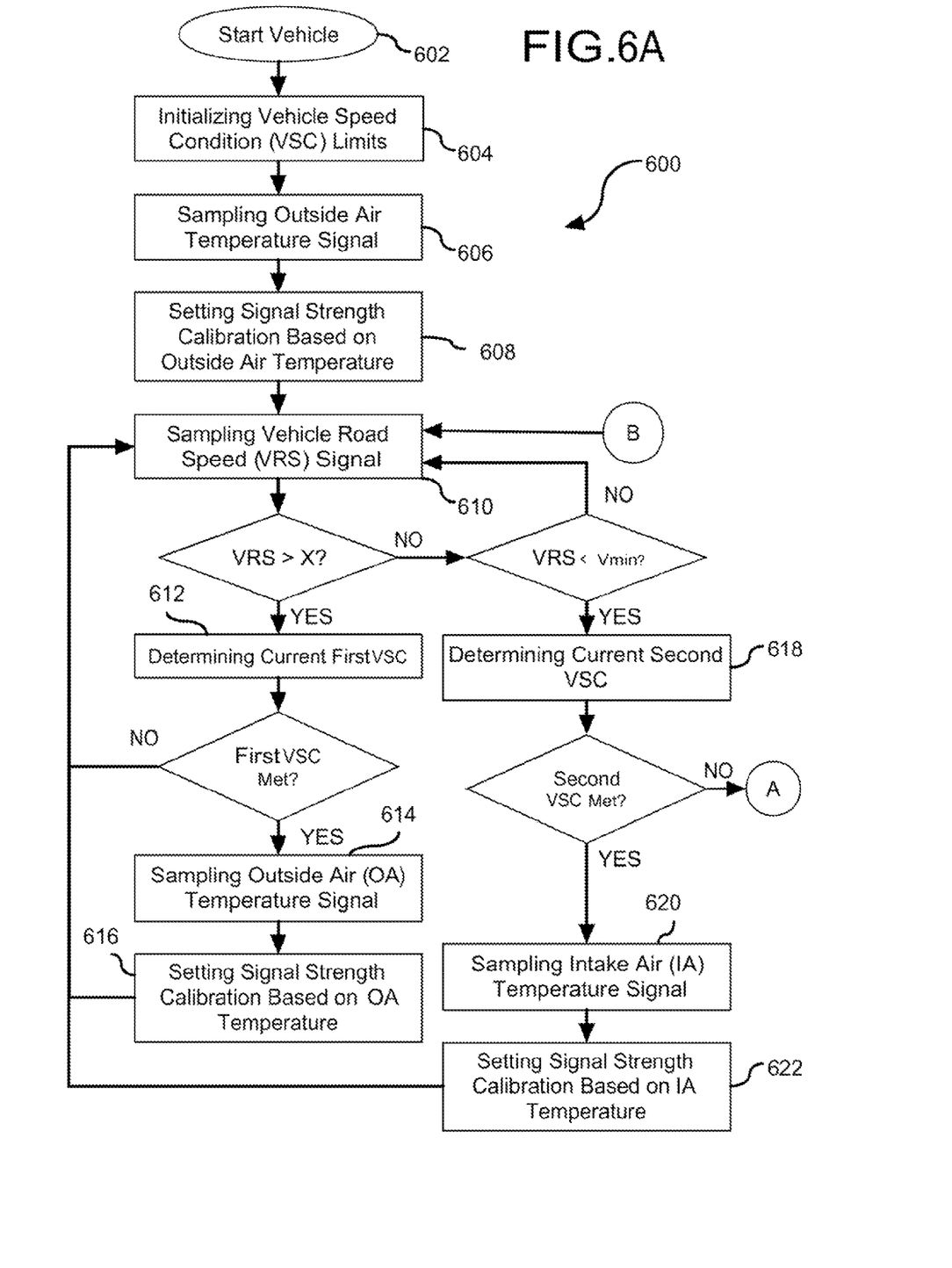
FIGS. 6A and 6B show a method for implementing ultrasonic sensor calibrating functionality in accordance with an embodiment of the inventive subject matter directed to a vehicle with an internal combustion engine in a running state.
Figure 6B:
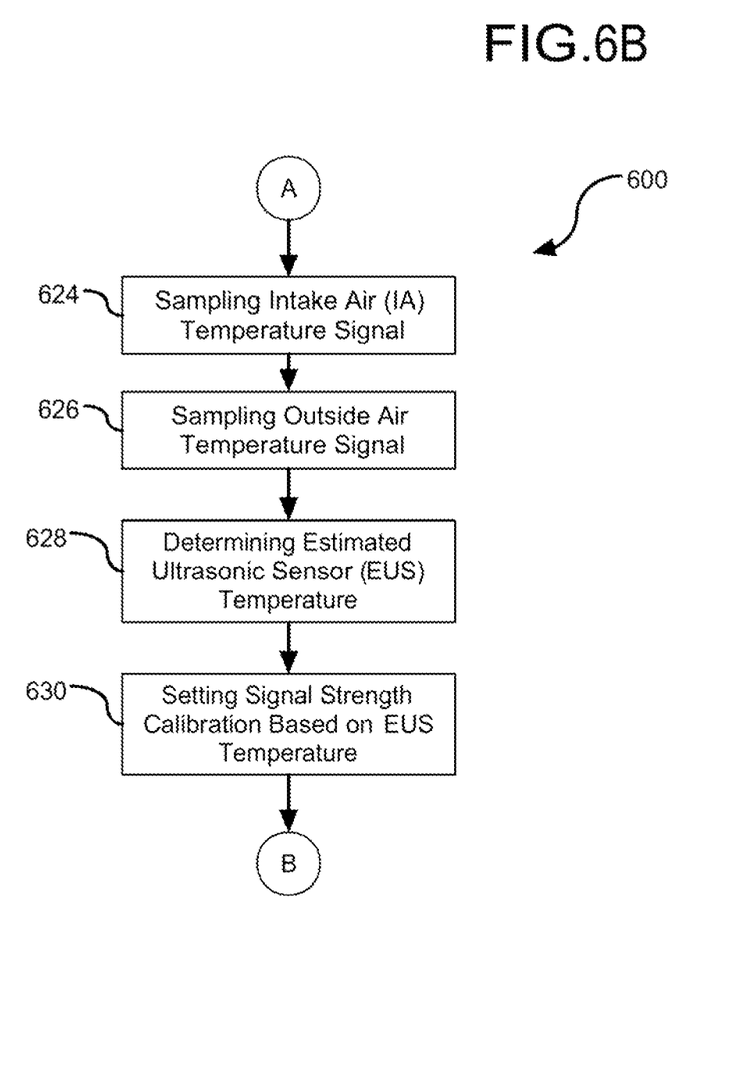

A method 600 for implementing ultrasonic sensor calibrating functionality is shown in FIGS. 6A and 6B. The method 600 allows a signal strength calibration used in determining a power output level of an object sensing signal from an ultrasonic sensor and/or used in processing an electrical signal outputted by the ultrasonic sensor in response to receiving a reflected portion of the object sensing signal (e.g., voltage indicating energy of a reflected acoustic signal) to be set (e.g., selected) dependent upon an estimated temperature of the ultrasonic sensor. Advantageously, the method 600 provides for a more accurate temperature of an ultrasonic sensor mounted in an environment of a vehicle that is subjected to excessive heat such as from an engine of a vehicle or pavement on which the vehicle is standing still. By more accurately determining the temperature of an ultrasonic sensor, it is possible to provide improved sensor performance as it relates to object detection and distance reporting. The method 600 is an example of an algorithm to estimate the ultrasonic sensor's temperature using various temperature information that is available from existing temperature sensors of the vehicle. In the specific example of an ultrasonic sensor that is mounted in or near an engine compartment of a vehicle and that is exposed to outside airflow when the vehicle is moving (e.g., mounted on a front bumper cover of the vehicle), an estimate of the ultrasonic sensor's temperature is made using a signal from an outside air temperature sensor and/or a signal from an intake air temperature sensor.

Referring to FIG. 6A, after an operation 602 is performed for starting the vehicle, an operation 604 is performed for initializing any vehicle speed condition (VSC) limits, as necessary. For example, as will be discussed below, some vehicle speed conditions can include counters and the like that need to be initialized at the onset of a current drive cycle or engine operation cycle. An operation 606 is then performed for sampling the signal from the outside air temperature sensor for determining a current outside air temperature, followed by an operation 608 being performed for setting a signal strength calibration based on the current outside air temperature (i.e., the temperature corresponding to the current outside air temperature sensor signal). This is an example of a first instance of a signal strength calibration. Setting the signal strength calibration can include setting (e.g., adjusting) calibration information associated with signal reception sensitivity, setting (e.g., adjusting) output power of an object sensing signal of the ultrasonic sensor, or both. For example, in addition to adjusting the signal strength calibration for signal reception (e.g., as discussed above in reference to FIGS. 3-5), output power of the ultrasonic sensor can be increased to maintain a uniform sound pressure level of the object sensing signal. Furthermore, it is disclosed herein that, in other embodiments, the operation 608 of setting the signal strength calibration could be based on a different air temperature (e.g., the intake air temperature).

After the signal strength calibration is set, an operation 610 is performed for sampling a vehicle road speed (VRS) signal for determining a current road speed of the vehicle. If the current vehicle road speed is less than a first vehicle speed threshold X (e.g., 30 mph) and is greater than a minimum vehicle speed threshold Vmin (e.g. 5 mph), the method 600 continues at the operation 610 for sampling the vehicle road speed (VRS) signal for determining a next instance of the current road speed of the vehicle. Otherwise, if the current vehicle road speed is greater than the first vehicle speed threshold X (e.g., 30 mph), an operation 612 is performed for determining a first vehicle speed condition based on the current vehicle road speed and the first vehicle speed threshold X. When the first vehicle speed condition is met, the method 600 continues with an operation 614 for sampling the signal from the outside air temperature sensor for determining a current outside air temperature and then an operation 616 is performed for setting the signal strength calibration based on the current outside air temperature (i.e., the temperature corresponding to the current outside air temperature sensor signal). This is an example of a second instance of the signal strength calibration. Otherwise, if the first vehicle speed condition is not met, the method 600 continues at the operation 610 for sampling the vehicle road speed (VRS) signal for determining a next instance of the current road speed of the vehicle.

The first vehicle speed condition allows certain assumptions about the current temperature of the ultrasonic sensor to be made. Through such assumptions, a signal strength calibration that enhances performance of the ultrasonic sensor at its current temperature can be set (e.g., selected from a plurality of available signal strength calibrations) and utilized in processing signal strength signals received by a signal processing unit, for example, from the ultrasonic sensor. In some embodiments of determining the first vehicle speed condition, a first counter is used for assessing how long the vehicle has been above the first vehicle speed threshold X (e.g. a counter that quantifies an aggregate time that the vehicle road speed is above the first vehicle speed threshold X). For example, each time the vehicle road speed is sampled and found to be above the first vehicle speed threshold X, this first counter is incremented by a given amount (e.g., +1). In this manner, the first counter can be used to confirm a vehicle speed condition in which a current speed of the vehicle has been greater than the first vehicle speed threshold for a duration of time longer than a first prescribed time threshold (e.g., a first time at-speed threshold) thereby supporting the signal strength calibration being set (e.g., selected from a plurality of available signal strength calibrations) based on a predefined temperature criteria such as, for example, the current outside air temperature. As will be discussed below in reference to a second vehicle speed threshold Vmin. a second counter that is used for assessing how long the vehicle has been below the second vehicle speed threshold Vmin is decremented by a given amount (e.g., −1) in response to the first counter being incremented. In this regard, the second counter quantifies an aggregate time that the vehicle road speed is below the second vehicle speed threshold Vmin. As necessary, the first and second counters can be reset to respective initial values and/or precluded from exceeding respective limits thereof.

Referring back to the operation 610 for sampling the vehicle road speed (VRS) signal for determining a next instance of the current road speed of the vehicle, if the current vehicle road speed is less than the first vehicle speed threshold X and is less than the minimum vehicle speed threshold Vmin, the method 600 continues at an operation 618 for determining a second vehicle speed condition based on the current vehicle road speed and the minimum vehicle speed threshold Vmin (i.e., a second vehicle speed threshold). When the second vehicle speed condition is met, the method 600 continues with an operation 620 for sampling the signal from the intake air temperature sensor for determining a current intake air temperature and then an operation 622 is performed for setting the signal strength calibration based on the current intake air temperature (i.e., the temperature corresponding to the intake air temperature signal). This is an example of a second instance of the signal strength calibration. Otherwise, as will be discussed below, the method 600 continues with implementing signal strength calibration based on an estimated temperature of the sensor as a function of both the outside air temperature and intake air temperature.

Similar to the first vehicle speed condition, the second vehicle speed condition allows certain assumptions about the current temperature of the ultrasonic sensor to be made. Through such assumptions, a signal strength calibration that enhances performance of the dultrasonic sensor at its current temperature can be set (e.g., selected from a plurality of available signal strength calibrations) and utilized in processing signal strength signals received by a signal processing unit, for example, from the ultrasonic sensor. As discussed above in the discussion relating to the first vehicle speed condition, in some embodiments of determining the second speed condition, a second counter is used for assessing how long the vehicle has been below the second vehicle speed threshold Vmin (e.g., a counter that quantifies an aggregate time that the vehicle road speed is below the second vehicle speed threshold Vmin). As previously disclosed above, each time the vehicle road speed is sampled and found to be below the second vehicle speed threshold Vmin, this second counter is incremented by a given amount (e.g., +1). In this manner, the second counter can be used to confirm a vehicle speed condition in which a current speed of the vehicle has been less than the second vehicle speed threshold for a duration of time longer than a second prescribed time threshold (e.g., a second time at-speed threshold) thereby supporting the signal strength calibration being set (e.g., selected) based on a predefined temperature criteria such as, for example, the current intake air temperature. In conjunction with incrementing the second counter, the first counter can also be decremented by a given amount (e.g., −1). For example, in the context of the flow diagram shown in FIG. 6A, when a counter corresponding to the first vehicle speed threshold X is increased a counter corresponding to the second vehicle speed threshold Vmin is correspondingly decreased and when the counter corresponding to the first vehicle speed threshold X is decreased the counter corresponding to the second vehicle speed threshold Vmin is correspondingly increased. In this regard, the counters jointly maintain criteria that define the first vehicle speed condition being met and the second vehicle speed condition being met.

As disclosed above and referring to FIG. 6B, the method 600 continues with setting the signal strength calibration based on an estimated temperature of the sensor as a function of both the outside air temperature and intake air temperature when neither the first nor second vehicle speed conditions are met. In this manner, a third vehicle speed condition is met when neither the first nor second vehicle speed conditions have been met. This third vehicle speed condition represents a transitional condition between a driving condition and a stopped/slow speed condition in which a current vehicle speed is below the first vehicle speed threshold X and is below the second vehicle speed threshold Vmin, but does not meet the second vehicle speed condition.

As shown in FIG. 68, setting the signal strength calibration based on an estimated temperature of the sensor as a function of both the outside air temperature and intake air temperature includes an operation 624 being performed for sampling the signal of the intake air temperature sensor and operation 626 being performed for sampling the signal of the outside air temperature sensor. The sequence in which such sampling is performed is not essential. It is disclosed herein that sampling the signal of the outside air temperature sensor (i.e. OAT) can include generating a composite OAT value that is a function of both an unfiltered OAT value (OAT-U) and a filtered OAT value (OAT-F). Proportioning of the unfiltered OAT value and the filtered OAT value can be based on considerations such as speed of the vehicle, time the vehicle has been at a given actual or average speed, etc. The filtered OAT value is a value that is generated using an algorithm to reduce the effect of underhood heat and road heat on ambient air temperature. This filtered OAT value is often already available to vehicle systems as it is used for displaying a stable OAT value (e.g., on a dashboard display) that does not exhibit short duration swings associated with proximity/exposure of the OAT sensor to underhood heat and road heat. The unfiltered (i.e., raw) OAT temperature value is that which represents the signal as outputted from the OAT sensor and from which the filtered OAT value is derived.

Thereafter, an operation 628 is performed for determining the estimated ultrasonic sensor temperature as a function of both the current intake air temperature (i.e., the temperature corresponding to the intake air temperature signal) and the current outside air temperature (i.e., the temperature corresponding to the outside air temperature signal). In one implementation, determining the ultrasonic sensor temperature includes determining a temperature offset as a function of the intake air temperature sensor signal and the outside air temperature sensor signal and then adding the temperature offset to a temperature corresponding to the outside air temperature sensor signal. One example of the temperature offset is the product between an offset constant (e.g., determined by experimentation for a given vehicle) and a difference between a temperature corresponding to the intake air temperature sensor signal and a temperature corresponding to the outside air temperature sensor signal. However, embodiments of the inventive subject matter are not unnecessarily limited to any particular approach for estimating the ultrasonic sensor temperature as a function of both the intake air temperature sensor signal (or a corresponding intake air temperature represented thereby) and the outside air temperature sensor signal (or a corresponding outside air temperature represented thereby).

It is disclosed herein that estimation of the ultrasonic sensor temperature can be based on information other than or in addition to the aforementioned air temperature sensor information. For example, estimation of the ultrasonic sensor temperature can be based on heat transfer calculations from powertrain components can be used. Information upon which such heat transfer calculations are a function include, but are not limited to, coolant temperature information, a combination of filtered outside air temperature information and unfiltered outside air temperature information (i.e., the composite OAT value), sun load information, climate control information, load/power information, road speed information, mile per gallon (MPG) booster radiator block engaged information, and the like. In this regard, embodiments of the inventive subject matter can utilize any and all available information available within an electronic controller system or other system of a vehicle to estimate ultrasonic sensor temperature.

In one specific example of implementing ultrasonic sensor calibrating functionality using information other than only air temperature sensor information, coolant temperature is used in along with outside air temperature and intake air temperature for setting signal strength calibration. Specifically, the operation 624 discussed above in reference to FIG. 6B is modified to perform an operation (or a plurality of operations) for sampling an intake air temperature signal and an engine coolant temperature signal (i.e., powertrain operating information) and the subsequent operation 628 is modified such that determining the estimated ultrasonic temperature is based on the intake air temperature signal, the engine coolant temperature signal and the OAT signal. Powertrain operating information used in setting thresholds can be determined under controlled conditions using a dynamometer. The sampled value corresponding to the OAT signal can be the aforementioned composite OAT value. Thus, at the operation 630, setting the signal strength calibration based on the estimated ultrasonic temperature will be based on the a value corresponding to the OAT temperature signal, a value corresponding to the coolant temperature signal, and a value corresponding to the intake air temperature signal. This is an example of a second instance of the signal strength calibration. For example, the signal strength calibration can be adjusted accordingly (i.e., for enhanced sensitivity) if the value corresponding to the OAT temperature signal is greater than an OAT Threshold, the value corresponding to the coolant temperature signal is greater than an engine coolant temp threshold and the value corresponding to the intake air temperature signal is greater than an intake air temperature threshold.

The intake air temperature value can be derived as a function of a greater proportion of outside ambient air temperature (i.e., from an IAT sensor) and a smaller proportion of engine compartment air temperature (e.g., from the OAT sensor). For example, depending on vehicle speed, the intake air temperature value can include mostly engine compartment at very slow speeds (indicative of engine bay temp) but at higher speeds reflects more outside air temp. If a vehicle is stopped or going slow, the coolant temp value can be weighted more heavily in estimating ultrasonic sensor temperature. The reverse is true for switching to a lower sensitivity threshold including an equation component to account for hysteresis. Such hysteresis component of the equation is included so that the system is not overly sensitive and thereby picking up ground reflections. The underlying objective of the manner in which ultrasonic sensor calibrations are set is to maintain threshold levels needed to see objects but not be so sensitive that it also sees ground reflections from road cracks, small rocks, etc.

It is well known that some vehicles have a radiator grille block that can be selectively closed for reducing aerodynamic draft and thereby increasing fuel efficiency (i.e., sometimes referred to as a mile per gallon (MPG) booster radiator block). Position (i.e., state) information of the actuator used to transition the radiator grille block between its open position (i.e. allowing air to flow freely through the grille such as when the vehicle is stationary) to its closed position (i.e., limiting airflow through the grille such as when the vehicle is travelling at a high rate of speed) can be used in estimating temperature of the ultrasonic sensor. For example if the vehicle is driven over a certain amount of speed with radiator grille block in its open position and with coolant temperature and OAT falling below their respective thresholds for a prescribed duration of time, it can be assumed that the ultrasonic sensor calibrations need to be switched back to baseline settings (i.e., for a baseline ultrasonic sensor temperature) as opposed to being set for enhanced sensitivity. To this end, the operation 624 discussed above in reference to FIG. 6B is modified such that sampling of the powertrain operating information further includes radiator grille block position duration of time. In this respect, cooling effect of the engine bay and thermal properties on the sensor are being assessed during a non-zero speed sensor soak with gas engine running as the intake air temperature signal becomes less accurate as an indicator of engine bay temperature after the vehicle has been moving for a period of time.

The abovementioned embodiments of the inventive subject matter are specifically configured for vehicles having an internal combustion engine in a running state under a hood of the vehicle. However, it is disclosed herein that the inventive subject matter can be embodied in a manner specifically configured for a full electric vehicle or for a hybrid electric vehicle having an engine that is not in a running state that would cause underhood heat of an amount that would affect ultrasonic temperature performance. In such embodiments, underhood heat is not a consideration.

Figure 7A:
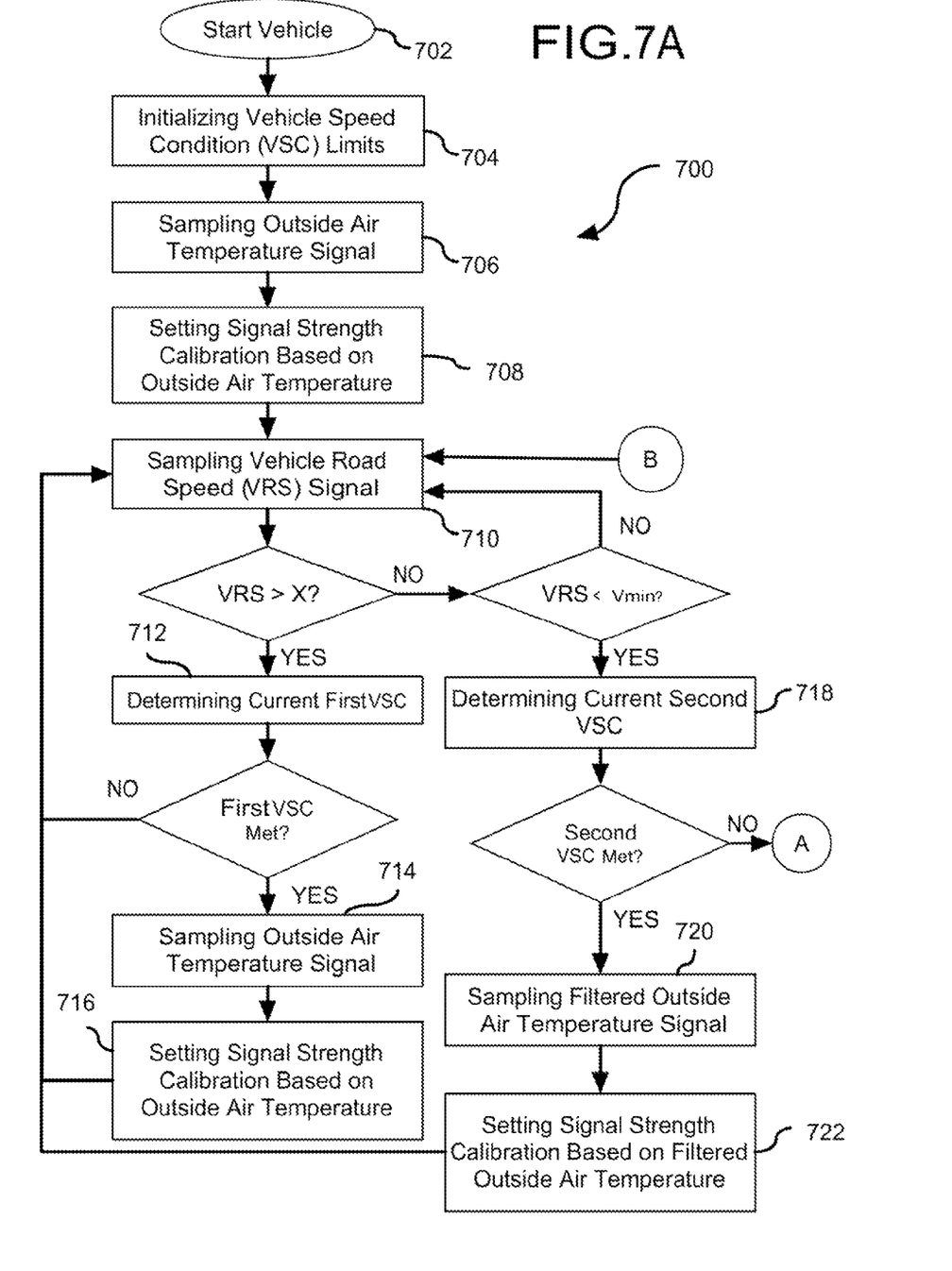
FIGS. 7A and 7B show a method for implementing ultrasonic sensor calibrating functionality in accordance with an embodiment of the inventive subject matter directed to a vehicle operating in an electric mode.
Figure 7B:
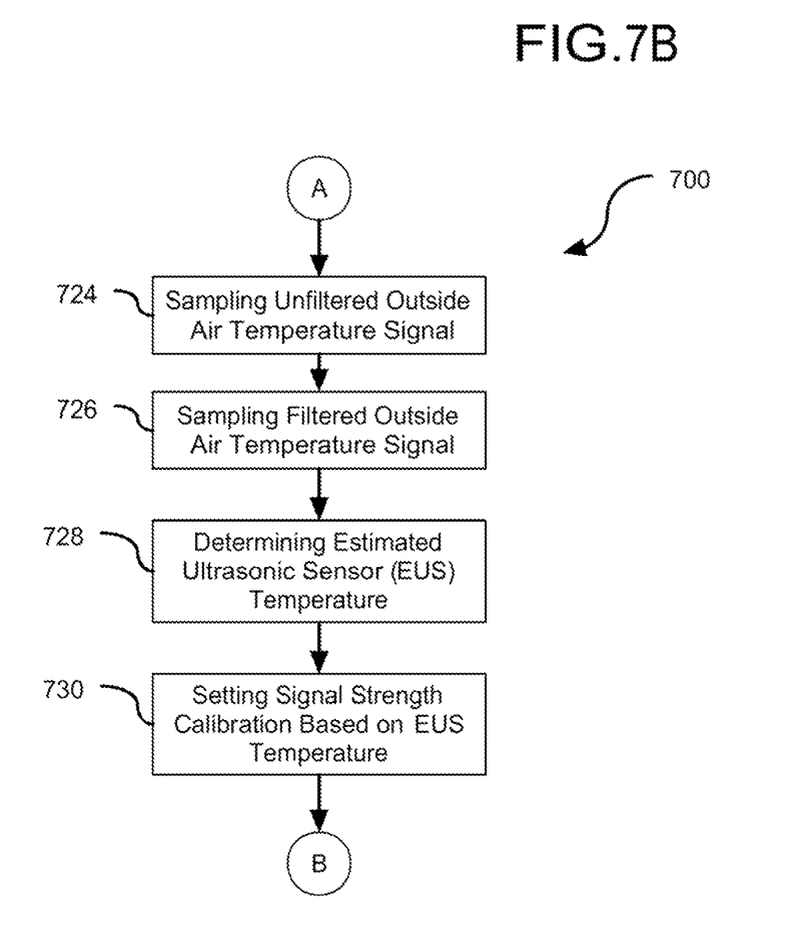

A method 700 for implementing ultrasonic sensor calibrating functionality in a vehicle running in an electric mode (e.g., a full electric vehicle or a plug-in hybrid) is shown in FIGS. 7A and 7B. The method 700 allows a signal strength calibration used in determining a power output level of an object sensing signal from an ultrasonic sensor and/or used in processing an electrical signal outputted by the ultrasonic sensor in response to receiving a reflected portion of the object sensing signal (e.g., voltage indicating energy of a reflected acoustic signal) to be set (e.g., selected) dependent upon an estimated temperature of the ultrasonic sensor. Advantageously, the method 700 provides for a more accurate temperature of an ultrasonic sensor mounted in an environment of a vehicle that is subjected to excessive heat such as from pavement on which the vehicle is travelling over. By more accurately determining the temperature of an ultrasonic sensor, it is possible to provide improved sensor performance as it relates to object detection and distance reporting. The method 700 is an example of an algorithm to estimate the ultrasonic sensor's temperature using various temperature information that is available from existing temperature sensors of the vehicle. In the specific example of an ultrasonic sensor that is exposed to outside airflow when the vehicle is moving (e.g., mounted on a front bumper cover of the vehicle), an estimate of the ultrasonic sensor's temperature is made using a signal from a signal representing an unfiltered outside air temperature and/or a signal representing a filtered outside air temperature.

Referring to FIG. 7A, after an operation 702 is performed for energizing the vehicle, an operation 704 is performed for initializing any vehicle speed condition (VSC) limits, as necessary. For example, as will be discussed below, some vehicle speed conditions can include counters and the like that need to be initialized at the onset of a current drive cycle or engine operation cycle. An operation 706 is then performed for sampling the signal from the outside air temperature sensor for determining a current unfiltered outside air temperature, followed by an operation 708 being performed for setting a signal strength calibration based on the current outside air temperature (i.e., the temperature corresponding to the raw current outside air temperature sensor signal). Setting the signal strength calibration can include setting (e.g., adjusting) calibration information associated with signal reception sensitivity, setting (e.g., adjusting) output power of an object sensing signal of the ultrasonic sensor, or both. For example, in addition to adjusting the signal strength calibration for signal reception (e.g., as discussed above in reference to FIGS. 3-5), output power of the ultrasonic sensor can be increased to maintain a uniform sound pressure level of the object sensing signal.

After the signal strength calibration is set, an operation 710 is performed for sampling a vehicle road speed (VRS) signal for determining a current road speed of the vehicle. If the current vehicle road speed is less than a first vehicle speed threshold X (e.g., 30 mph) and is greater than a minimum vehicle speed threshold Vmin (e.g., 5 mph), the method 700 continues at the operation 710 for sampling the vehicle road speed (VRS) signal for determining a next instance of the current road speed of the vehicle. Otherwise, if the current vehicle road speed is greater than the first vehicle speed threshold X (e.g., 30 mph), an operation 712 is performed for determining a first vehicle speed condition based on the current vehicle road speed and the first vehicle speed threshold X. When the first vehicle speed condition is met, the method 700 continues with an operation 714 for sampling the signal from the outside air temperature sensor for determining a current unfiltered outside air temperature and then an operation 716 is performed for setting the signal strength calibration based on the current outside air temperature (i.e., the temperature corresponding to the current raw outside air temperature sensor signal). Otherwise, if the first vehicle speed condition is not met, the method 700 continues at the operation 710 for sampling the vehicle road speed (VRS) signal for determining a next instance of the current road speed of the vehicle. It is disclosed herein that the outside air temperature of the operations 706, 708, 712 and 714 can be raw outside air temperature signal that has been processed such as, for example with certain diagnostic plausibility checks, rules, etc thereby producing is lightly filtered (i.e., a baseline processed outside air temperature signal) in regard to a more highly filtered outside air temperature signal as discussed below.

The first vehicle speed condition allows certain assumptions about the current temperature of the ultrasonic sensor to be made. Through such assumptions, a signal strength calibration that enhances performance of the ultrasonic sensor at its current temperature can be set (e.g., selected from a plurality of available signal strength calibrations) and utilized in processing signal strength signals received by a signal processing unit, for example, from the ultrasonic sensor. In some embodiments of determining the first vehicle speed condition, a first counter is used for assessing how long the vehicle has been above the first vehicle speed threshold X (e.g., a counter that quantifies an aggregate time that the vehicle road speed is above the first vehicle speed threshold X). For example, each time the vehicle road speed is sampled and found to be above the first vehicle speed threshold X, this first counter is incremented by a given amount (e.g., +1). In this manner, the first counter can be used to confirm a vehicle speed condition in which a current speed of the vehicle has been greater than the first vehicle speed threshold for a duration of time longer than a first prescribed time threshold (e.g., a first time at-speed threshold) thereby supporting the signal strength calibration being set (e.g., selected from a plurality of available signal strength calibrations) based on a predefined temperature criteria such as, for example, the current outside air temperature. As will be discussed below in reference to a second vehicle speed threshold Vmin, a second counter that is used for assessing how long the vehicle has been below the second vehicle speed threshold Vmin is decremented by a given amount (e.g., −1) in response to the first counter being incremented. In this regard, the second counter quantifies an aggregate time that the vehicle road speed is below the second vehicle speed threshold Vmin. As necessary, the first and second counters can be reset to respective initial values and/or precluded from exceeding respective limits thereof.

Referring back to the operation 710 for sampling the vehicle road speed (VRS) signal for determining a next instance of the current road speed of the vehicle, if the current vehicle road speed is less than the first vehicle speed threshold X and is less than the minimum vehicle speed threshold Vmin, the method 700 continues at an operation 718 for determining a second vehicle speed condition based on the current vehicle road speed and the minimum vehicle speed threshold Vmin (i.e., a second vehicle speed threshold). When the second vehicle speed condition is met, the method 700 continues with an operation 720 for sampling a signal providing a filtered representation of the outside air temperature (i.e., the filtered outside air temperature) for determining a current filtered outside air temperature and then an operation 722 is performed for setting the signal strength calibration based on the current filtered outside air temperature. Otherwise, as will be discussed below, the method 700 continues with implementing signal strength calibration based on an estimated temperature of the sensor as a function of both the unfiltered outside air temperature and filtered outside air temperature. It is disclosed herein that the operation for sampling the signal providing the filtered representation of the outside air temperature can be replaced with an operation for deriving the filtered representation of the outside air temperature using the unfiltered outside air temperature signal.

Similar to the first vehicle speed condition, the second vehicle speed condition allows certain assumptions about the current temperature of the ultrasonic sensor to be made. Through such assumptions, a signal strength calibration that enhances performance of the ultrasonic sensor at its current temperature can be set (e.g., selected from a plurality of available signal strength calibrations) and utilized in processing signal strength signals received by a signal processing unit, for example, from the ultrasonic sensor. As discussed above in the discussion relating to the first vehicle speed condition, in some embodiments of determining the second speed condition, a second counter is used for assessing how long the vehicle has been below the second vehicle speed threshold Vmin (e.g., a counter that quantifies an aggregate time that the vehicle road speed is below the second vehicle speed threshold Vmin). As previously disclosed above, each time the vehicle road speed is sampled and found to be below the second vehicle speed threshold Vmin. this second counter is incremented by a given amount (e.g., +1). In this manner, the second counter can be used to confirm a vehicle speed condition in which a current speed of the vehicle has been less than the second vehicle speed threshold for a duration of time longer than a second prescribed time threshold (e.g., a second time at-speed threshold) thereby supporting the signal strength calibration being set (e.g., selected) based on a predefined temperature criteria such as, for example, the current intake air temperature. In conjunction with incrementing the second counter, the first counter can also be decremented by a given amount (e.g., −1). For example, in the context of the flow diagram shown in FIG. 7A, when a counter corresponding to the first vehicle speed threshold X is increased a counter corresponding to the second vehicle speed threshold Vmin is correspondingly decreased and when the counter corresponding to the first vehicle speed threshold X is decreased the counter corresponding to the second vehicle speed threshold Vmin is correspondingly increased. In this regard, the counters jointly maintain criteria that define the first vehicle speed condition being met and the second vehicle speed condition being met.

As disclosed above and referring to FIG. 7B, the method 700 continues with setting the signal strength calibration based on an estimated temperature of the sensor as a function of both the unfiltered outside air temperature and filtered outside air temperature when neither the first nor second vehicle speed conditions are met. In this manner, a third vehicle speed condition is met when neither the first nor second vehicle speed conditions have been met. This third vehicle speed condition represents a transitional condition between a driving condition and a stopped/slow speed condition in which a current vehicle speed is below the first vehicle speed threshold X and is below the second vehicle speed threshold Vmin, but does not meet the second vehicle speed condition.

As shown in FIG. 7B, setting the signal strength calibration based on an estimated temperature of the sensor as a function of both the unfiltered outside air temperature and filtered outside air temperature includes an operation 724 being performed for sampling the unfiltered outside air temperature signal and operation 726 being performed for sampling the filtered outside air temperature signal (or otherwise determining the filtered outside air temperature). The sequence in which such sampling is performed is not essential. Thereafter, an operation 728 is performed for determining the estimated ultrasonic sensor temperature as a function of both the unfiltered outside air temperature and the filtered outside air temperature. In this regard, a composite outside air temperature value that is a function of both the unfiltered outside air temperature and the filtered outside air temperature is generated. Proportioning of the unfiltered outside air temperature and the filtered outside air temperature can be based on considerations such as speed of the vehicle, time the vehicle has been at a given actual or average speed, etc. The filtered outside air temperature can be a value that is generated using an algorithm to reduce the effect of road heat on ambient air temperature. A signal representing this filtered outside air temperature is often already available to vehicle systems as it is used for displaying a stable outside air temperature value (e.g., on a dashboard display) that does not exhibit short duration swings associated with proximity/exposure of the outside air temperature sensor to road heat. The unfiltered (i.e., raw) outside air temperature value is that which represents the signal as outputted from the outside air temperature sensor and from which the filtered outside air temperature value is derived.

In the preceding detailed description, reference has been made to the accompanying drawings that form a part hereof, and in which are shown by way of illustration specific embodiments in which the inventive subject matter may be practiced. These embodiments, and certain variants thereof, have been described in sufficient detail to enable those skilled in the art to practice embodiments of the inventive subject matter. It is to be understood that other suitable embodiments may be utilized and that logical, mechanical, chemical and electrical changes may be made without departing from the spirit or scope of such inventive disclosures. To avoid unnecessary detail, the description omits certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. An electronic controller system of a vehicle having at least one data processing device coupled between an ultrasonic sensor, a signaling apparatus configured for outputting outside air temperature information and a signaling apparatus configured for outputting powertrain operating information, comprising:

instructions causing the at least one data processing device to determine a first instance of a signal strength calibration, the first instance of the signal strength calibration is based on a first instance of outside air temperature information and a first instance of powertrain operating information and the signal strength calibration enables information outputted from the ultrasonic sensor to provide at least a baseline level of object detecting performance;

instructions causing the at least one data processing device to determine a vehicle operating condition requiring alteration of the signal strength calibration for maintaining at least the baseline level of object detecting performance from the information outputted from the ultrasonic sensor; and instructions causing the at least one data processing device to determine a second instance of the signal strength calibration in response to determining the vehicle operating condition requiring alteration of the signal strength calibration, the second instance of the signal strength calibration is based on at least one of a second instance of the outside air temperature information and a second instance of the powertrain operating information and the second instance of the signal strength calibration enables the information outputted from the ultrasonic sensor to provide at least the baseline level of object detecting performance.

2. The system of claim 1 wherein each one of the instances of the signal strength calibration includes respective calibration information associated with signal reception sensitivity and respective calibration information associated with output power of an object sensing signal of the ultrasonic sensor.

3. The system of claim 2 wherein at least one of:
the calibration information associated with signal reception sensitivity for the second instance of the signal strength calibration providing for greater object sensing sensitivity than the calibration information associated with signal reception sensitivity for the first instance of the signal strength calibration; and
the calibration information associated with the output power of the object sensing signal for the second instance of the signal strength calibration providing for greater object sensing sensitivity than the calibration information associated with the output power of the object sensing signal for the first instance of the signal strength calibration.

4. The system of claim 2 wherein the outside air temperature information includes a composite outside air temperature value that is a function of both an unfiltered outside air temperature value and a filtered outside air temperature value.

5. The system of claim 1 wherein the vehicle operating condition includes at least one of:
a current outside air temperature that adversely impacts an ability of the information outputted from the ultrasonic sensor to provide at least the baseline level of object detecting performance; and
a current powertrain operating parameter that adversely impacts an ability of the information outputted from the ultrasonic sensor to provide at least the baseline level of object detecting performance.

6. The system of claim 1 wherein the outside air temperature information includes a composite outside air temperature value that is a function of both an unfiltered outside air temperature value and a filtered outside air temperature value.

7. The system of claim 6 wherein proportioning of the unfiltered outside air temperature value and the filtered outside air temperature value is a function of at least a portion of the powertrain operating information.

8. The system of claim 7 wherein the vehicle operating condition includes at least one of:
a current outside air temperature that adversely impacts an ability of the information outputted from the ultrasonic sensor to provide at least the baseline level of object detecting performance; and
a current powertrain operating parameter that adversely impacts an ability of the information outputted from the ultrasonic sensor to provide at least the baseline level of object detecting performance.

9. The system of claim 6 wherein each one of the instances of the signal strength calibration includes respective calibration information associated with signal reception sensitivity and respective calibration information associated with output power of an object sensing signal of the ultrasonic sensor.

10. The system of claim 9 wherein at least one of:
the calibration information associated with signal reception sensitivity for the second instance of the signal strength calibration providing for greater object sensing sensitivity than the calibration information associated with signal reception sensitivity for the first instance of the signal strength calibration; and
the calibration information associated with the output power of the object sensing signal for the second instance of the signal strength calibration providing for greater object sensing sensitivity than the calibration information associated with the output power of the object sensing signal for the first instance of the signal strength calibration.

11. The system of claim 10 wherein the vehicle operating condition includes at least one of:
a current outside air temperature that adversely impacts an ability of the information outputted from the ultrasonic sensor to provide at least the baseline level of object detecting performance; and
a current powertrain operating parameter that adversely impacts an ability of the information outputted from the ultrasonic sensor to provide at least the baseline level of object detecting performance.

12. A method for processing a signal provided from an ultrasonic sensor of a vehicle to a signal processing unit of the vehicle, comprising the steps of:
providing the signal processing unit with a first instance of a signal strength calibration, the first instance of the signal strength calibration is based on a first instance of outside air temperature information and a first instance of powertrain operating information and the signal strength calibration enables information outputted from the ultrasonic sensor to provide at least a baseline level of object detecting performance;
determining a vehicle operating condition requiring alteration of the signal strength calibration for maintaining at least the baseline level of object detecting performance from the information outputted from the ultrasonic sensor; and
providing the signal processing unit with a second instance of the signal strength calibration in response to determining the vehicle operating condition requiring alteration of the signal strength calibration, the second instance of the signal strength calibration is based on at least one of a second instance of the outside air temperature information and a second instance of the powertrain operating information and the second instance of the signal strength calibration enables the information outputted from the ultrasonic sensor to provide at least the baseline level of object detecting performance.

13. The method of claim 12 wherein each one of the instances of the signal strength calibration includes respective calibration information associated with signal reception sensitivity and respective calibration information associated with output power of an object sensing signal of the ultrasonic sensor.

14. The method of claim 12 wherein the outside air temperature information includes a composite outside air temperature value that is a function of both an unfiltered outside air temperature value and a filtered outside air temperature value.

15. The method of claim 12 wherein the vehicle operating condition includes at least one of:
a current outside air temperature that adversely impacts an ability of the information outputted from the ultrasonic sensor to provide at least the baseline level of object detecting performance; and
a current powertrain operating parameter that adversely impacts an ability of the information outputted from the ultrasonic sensor to provide at least the baseline level of object detecting performance.

16. The method of claim 14 wherein proportioning of the unfiltered outside air temperature value and the filtered outside air temperature value is a function of at least a portion of the powertrain operating information.

17. A vehicle, comprising:
an ultrasonic sensor;
a first signaling apparatus configured for outputting outside air temperature information; a
a second signaling apparatus configured for outputting powertrain operating information; and
a signal processing unit coupled between the ultrasonic sensor, the first signaling apparatus and the second signaling apparatus, the signal processing unit includes at least one data processing device a set of instructions configured for causing the at least one data processing device to carry out operations for:
determining a first instance of a signal strength calibration, the first instance of the signal strength calibration is based on a first instance of outside air temperature information and a first instance of powertrain operating information and the signal strength calibration enables information outputted from the ultrasonic sensor to provide at least a baseline level of object detecting performance;
determining a vehicle operating condition requiring alteration of the signal strength calibration for maintaining at least the baseline level of object detecting performance from the information outputted from the ultrasonic sensor; and
determining a second instance of the signal strength calibration in response to determining the vehicle operating condition requiring alteration of the signal strength calibration, the second instance of the signal strength calibration is based on at least one of a second instance of the outside air temperature information and a second instance of the powertrain operating information and the second instance of the signal strength calibration enables the information outputted from the ultrasonic sensor to provide at least the baseline level of object detecting performance.

18. The vehicle of claim 17 wherein each one of the instances of the signal strength calibration includes respective calibration information associated with signal reception sensitivity and respective calibration information associated with output power of an object sensing signal of the ultrasonic sensor.

19. The vehicle of claim 17 wherein the outside air temperature information includes a composite outside air temperature value that is a function of both an unfiltered outside air temperature value and a filtered outside air temperature value.

20. The vehicle of claim 17 wherein the vehicle operating condition includes at least one of:

a current outside air temperature that adversely impacts an ability of the information outputted from the ultrasonic sensor to provide at least the baseline level of object detecting performance; and a current powertrain operating parameter that adversely impacts an ability of the information outputted from the ultrasonic sensor to provide at least the baseline level of object detecting performance.

21. The vehicle of claim 17 wherein the powertrain operating information includes coolant temperature information, intake air temperature information, grille block position information, and vehicle speed information.

22. The vehicle of claim 21 wherein each one of the instances of the signal strength calibration includes respective calibration information associated with signal reception sensitivity and respective calibration information associated with output power of an object sensing signal of the ultrasonic sensor.

23. The vehicle of claim 21 wherein the outside air temperature information includes a composite outside air temperature value that is a function of both an unfiltered outside air temperature value and a filtered outside air temperature value.

24. The vehicle of claim 21 wherein the vehicle operating condition includes at least one of:

a current outside air temperature that adversely impacts an ability of the information outputted from the ultrasonic sensor to provide at least the baseline level of object detecting performance; and a current powertrain operating parameter that adversely impacts an ability of the information outputted from the ultrasonic sensor to provide at least the baseline level of object detecting performance.

* * * * *